(12) United States Patent
Boyer et al.

(10) Patent No.: US 12,245,948 B2
(45) Date of Patent: Mar. 11, 2025

(54) BONE FUSION PLATE AND SYSTEM AND METHOD FOR ITS USE IN THE WRIST

(71) Applicant: Exsomed Corporation, Aliso Viejo, CA (US)

(72) Inventors: Martin Boyer, St. Louis, MO (US); Andrew Leither, Akron, OH (US); Kathleen McKeon, Birmingham, AL (US); Kulvinder Sachar, Denver, CO (US); Michael Zwolinski, Willoughby, OH (US)

(73) Assignee: ExsoMed Corporation, Aliso Viejo, CA (US)

( * ) Notice: Subject to any disclaimer, the term of this patent is extended or adjusted under 35 U.S.C. 154(b) by 155 days.

(21) Appl. No.: 17/811,999

(22) Filed: Jul. 12, 2022

(65) Prior Publication Data

US 2023/0063432 A1 Mar. 2, 2023

Related U.S. Application Data

(62) Division of application No. 16/380,561, filed on Apr. 10, 2019, now Pat. No. 11,413,155.

(Continued)

(51) Int. Cl.
*A61B 17/80* (2006.01)
*A61B 17/86* (2006.01)
(Continued)

(52) U.S. Cl.
CPC ............ *A61F 2/4261* (2013.01); *A61B 17/80* (2013.01); *A61B 17/8014* (2013.01); *A61B 17/8019* (2013.01); *A61B 17/8052* (2013.01); *A61B 17/8061* (2013.01); *A61B 17/86* (2013.01); *A61B 17/8866* (2013.01); *A61B 17/8057* (2013.01); *A61B 17/8605* (2013.01);
(Continued)

(58) Field of Classification Search
CPC .................. A61F 2/4261; A61B 17/8014; A61B 17/8061
See application file for complete search history.

(56) References Cited

U.S. PATENT DOCUMENTS

| 2007/0270850 | A1 | 11/2007 | Geissler |
| 2017/0216043 | A1 | 8/2017 | Surma et al. |
| 2019/0175236 | A1* | 6/2019 | Blacklidge ......... A61B 17/1682 |

FOREIGN PATENT DOCUMENTS

KR 10-2013-0069578 A 6/2013

OTHER PUBLICATIONS

International Search Report and Written Opinion in corresponding International Patent Application No. PCT/US2021/030162, dated Aug. 17, 2021, 11 pages.

* cited by examiner

*Primary Examiner* — Olivia C Chang
(74) *Attorney, Agent, or Firm* — K&L Gates LLP

(57) ABSTRACT

The present invention relates to a crescent or tri-corner shaped orthopedic plate with at least a first and a second end, and generally coextensive top and bottom surfaces joined directly or indirectly by an edge. The plate includes a plurality of fixation holes the first end of the plate and a second end of the plate that receives locking screws and intermediate the two holes, the plate includes a recess that defines a screw hole edge at an angle relative to the top surface of the plate so as to receive and support a screw in the recess. The invention further relates to a method of fusion using the plate and a clamp designed for the method.

15 Claims, 12 Drawing Sheets

Related U.S. Application Data

(60) Provisional application No. 62/655,530, filed on Apr. 10, 2018.

(51) Int. Cl.
*A61B 17/88* (2006.01)
*A61F 2/42* (2006.01)
*A61F 2/30* (2006.01)

(52) U.S. Cl.
CPC ............... *A61F 2002/30604* (2013.01); *A61F 2002/4264* (2013.01); *A61F 2002/4271* (2013.01)

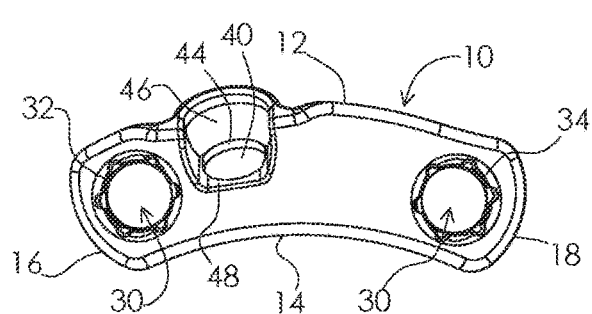
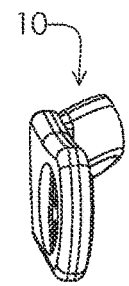
FIG. 1    FIG. 2
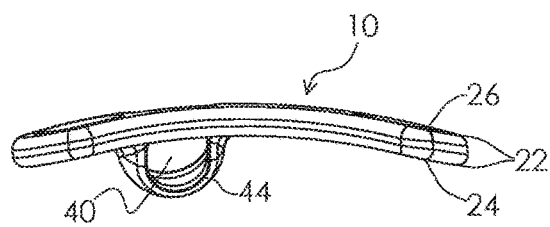
FIG. 3
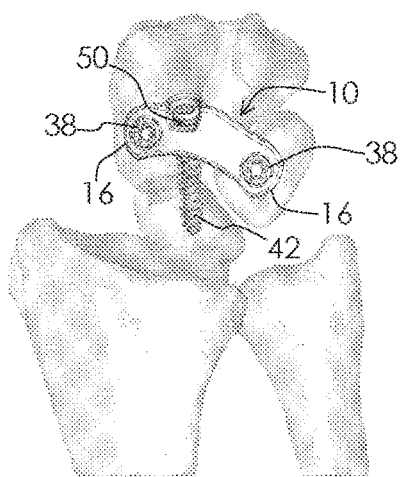
FIG. 4

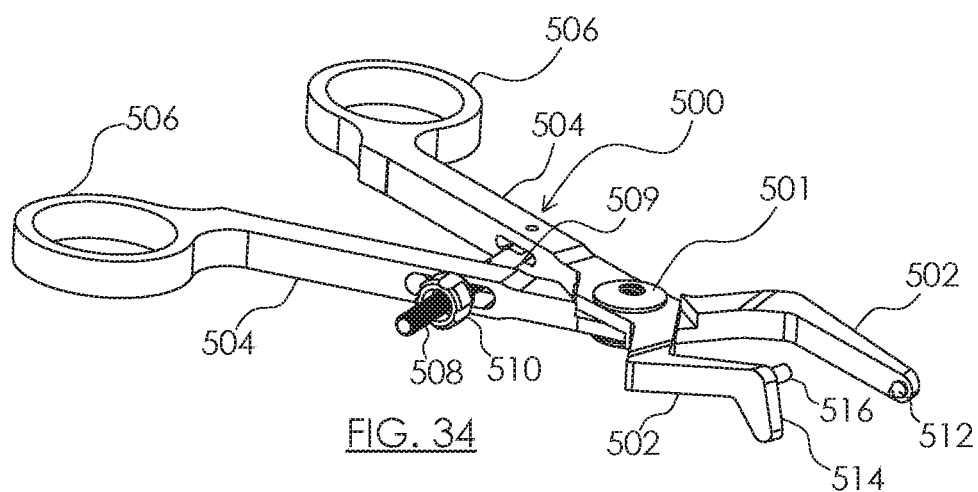
FIG. 34
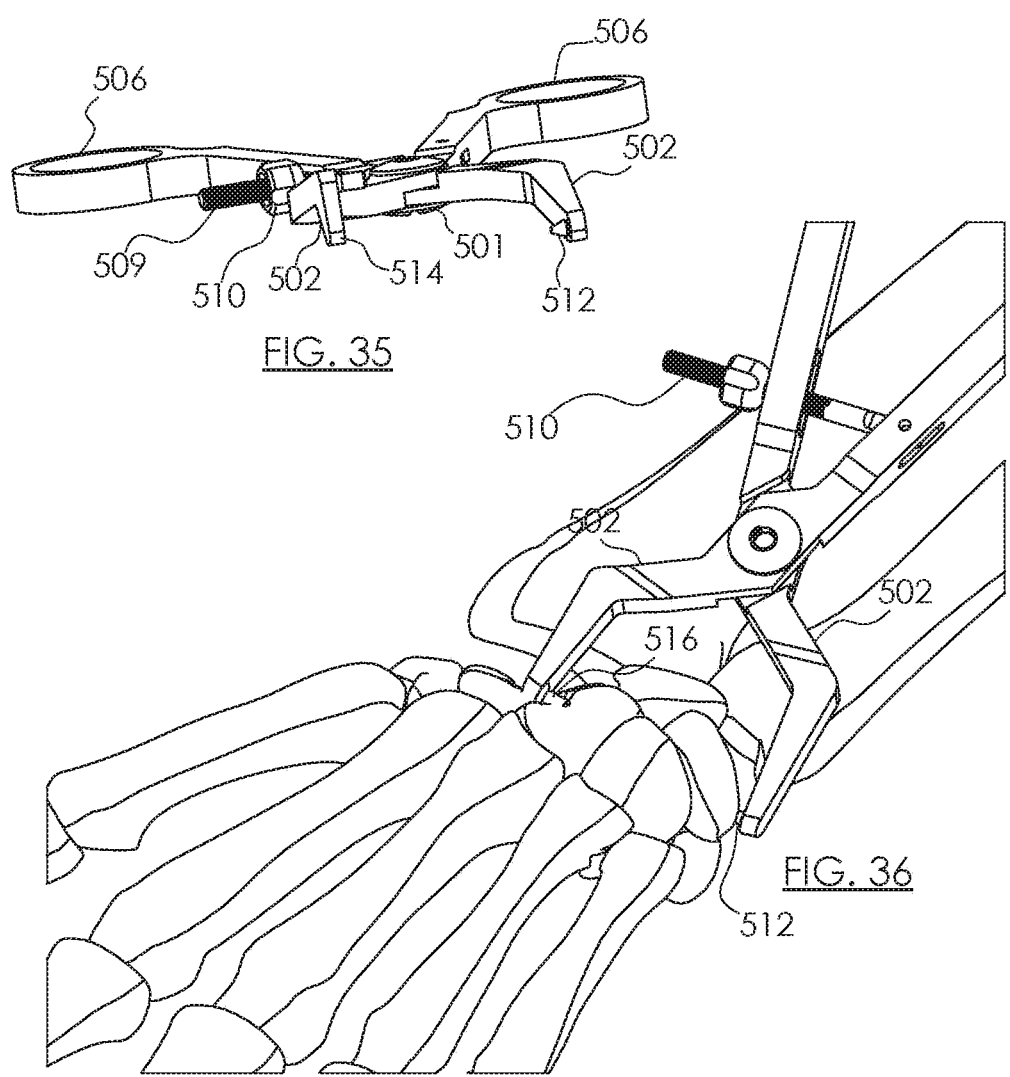
FIG. 35
FIG. 36

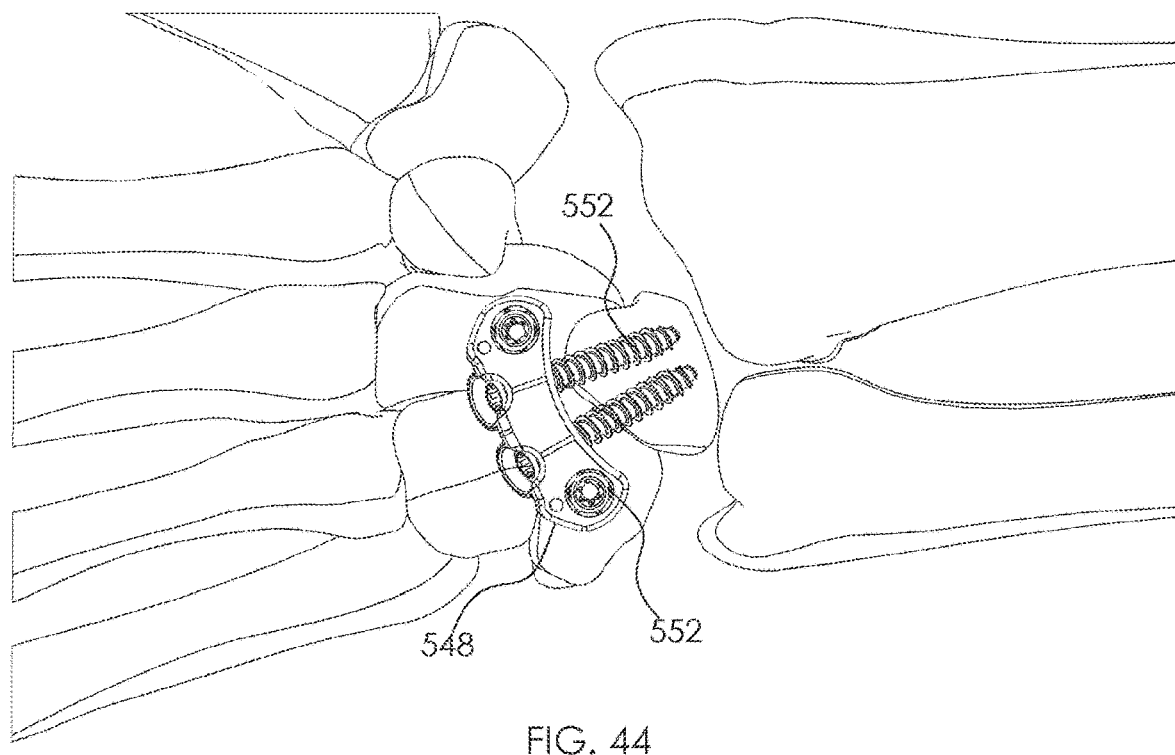
FIG. 44
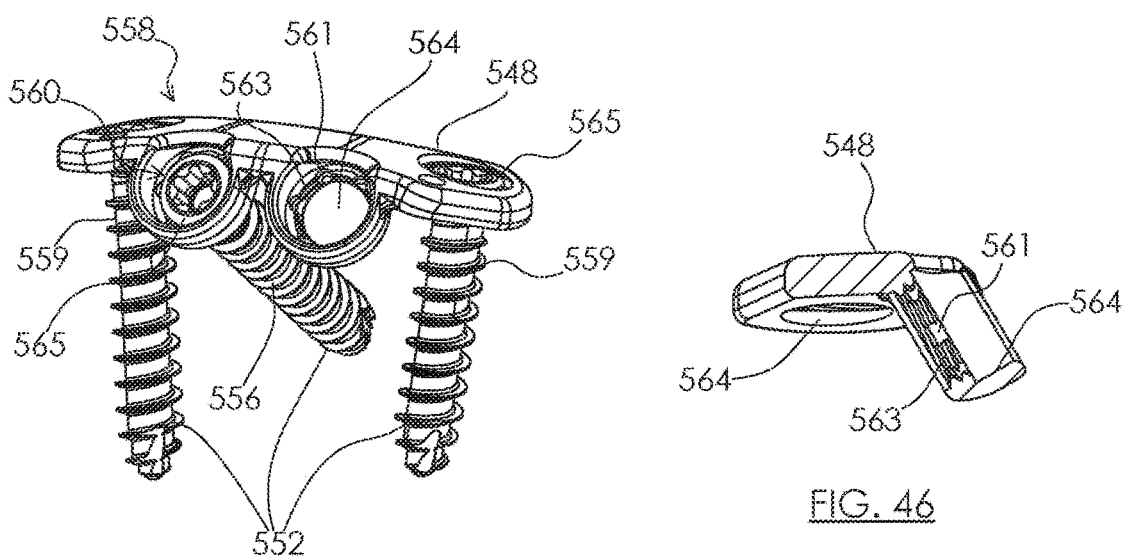
FIG. 45
FIG. 46
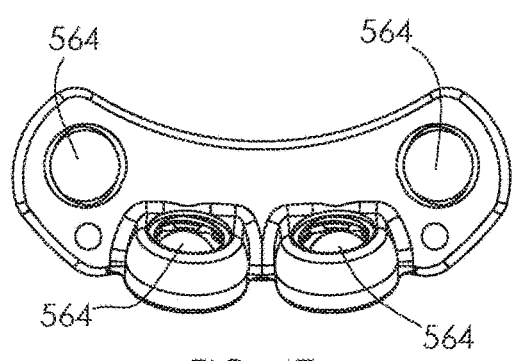
FIG. 47

BONE FUSION PLATE AND SYSTEM AND METHOD FOR ITS USE IN THE WRIST

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

FIELD OF THE INVENTION

The present invention relates to orthopedic implants and to methods of using the implants in surgical procedures in which the implant system is designed for fusion of the carpal bones of the human wrist.

BACKGROUND OF THE INVENTION

The wrist is composed of a number of bones, called the carpal bones that articulate relative to each other to support the palm of the hand and allow the complicated sliding and hinged movements which are unique to primate hands. The carpals are arranged in a distal row, nearer the radius and ulna, and a proximal row, nearer the metacarpals. The proximal row is found at the level of the distal wrist crease and includes the scaphoid, lunate, triquetrum, and pisiform. The second row of carpal bones, the distal row, is made up of the trapezium, trapezoid, capitate, and hamate; the distal row articulates with the bases of the five metacarpal bones.

The wrist is a sophisticated and vulnerable joint, prone to both injury, such as a fall on an out-stretched hand, and to degenerative disease, such as osteoarthritis.

One of the most prevalent arthritic disease patterns in the wrist is Scapholunate advanced collapse commonly known as "SLAC" and marked by a scaphoid or scapholunate ligament injury with collapse on the radial side of the wrist. The distal radius has two articular fossae, one of which is spoon-like with an elliptical profile that narrows toward the radial styloid in a dorsal-volar plane, for the scaphoid, and the other of which is spherical for the moon-shaped lunate. The result of injury to the scaphoid bone or its supporting structure is often radial side collapse and flexion of the scaphoid, which causes a mis-alignment of the radioscaphoid joint. This causes functional and neurological problems over time.

A solution to this indication is surgical intervention with a fusion of the carpal bones of the wrist and a reduction of the lunate relative to the radius. The prior art has provided hardware to maintain the re-aligned bones, including wires, screws, and plates, with a hub-cap type plate representing a typical solution. However, this solution also requires reaming a substantial amount of bone such that the topography of the plate can be accepted in the dorsal portion of the back of the hand, which typically has very little adipose tissue to cover any prosthetic hardware, particularly in a senior population.

SUMMARY OF THE INVENTION

The present invention relates to a dorsal wrist implant and method for its use for a fusion typically known as a "four corner fusion", which is used for indications including osteoarthritis, rheumatoid arthritis, avascular necrosis of the scaphoid, mid-carpal instability, intra-articular fractures involving the carpal joints, Kienbock disease, capitolunate degeneration, ligamentary dissociation, and crystalline deposition disorders, such as gout, and calcium pyrophosphate dehydrate deposition disease (CPPD), and other radial-side wrist pathologies.

The implant of the present invention is a plate having a crescent or kidney shaped outline in a first embodiment (i.e. a plate having an arcuate foot-print marked by coextensive top and bottom surfaces defining an outline comprising two concentric curved long sides, one convex and one concave, joining two rounded short sides) and a uniform through thickness through-out at least half of the surface area of its body and co-planar top and bottom surfaces. These surfaces are perforated by one or more (preferably 3 or 4) through openings which are preferably located within the rounded opposing short sides and are threaded so as to accept locking or non-locking screws) of appropriate length (i.e. 2-3 cm), width (i.e. 0.5-2 cm) and thickness (i.e. 1-3 mm). In a further embodiment, the plate has a tri-corner shape which has the arcuate shape and further including a third end centered in the convex side between the first and second ends.

More particularly, the invention relates to a crescent shaped plate having coextensive top and bottom surface and including opposing ends which include screw holes defined by internally threaded and tapered openings within the top and bottom surfaces. These openings are capable of receiving fixed or variable locking screws or variable screws. The plate further includes one or more intermediate offset recess including an opening which is not within the top or bottom surface of the plate and which is positioned to receive a lag screw such that it is capable of drawing a bone or bone fragment in the direction of the bottom central surface of the plate. Also of advantage is that, the off-set holes include pendulous rim members that project downward from the bottom surface of the plate body and which defined by the side walls of the recess which surround these screw holes. These rim members thus form "teeth" which bite into countersunk recesses in the bone that they overlie, and specifically, the hamate bone so as to help hold it in position without the need for an additional screw.

The plate is provided in several different configurations. In all embodiments, the plate includes a compression recess as described, which is sunk below or angled relative to the top surface (i.e. the side which would face away from the bone in use). The compression recess(es) houses one or more screw openings located in a plane that does not lie within the top or bottom surface of the plate (and which does not extend normal to these surfaces through the plate) and that receives and supports one or more screws (typically self-tapping, locking or non-locking, threaded cancellous screws of from 10 to 40 mm in length), such as a lag screw, at an oblique angle relative to the plane defined at the top surface of the plate surrounding the opening within the top surface to receive the screw.

The recess and the opening are positioned so that a screw captured therein draws an associated bone or bone fragment toward that central bottom surface of the plate. This screw can be used for the passive reduction of a bone or bone fragment, often preferably, the lunate in wrist fusion procedures in accordance with a novel procedure of wrist fusion. The procedure also involves a unique clamp that has a locking scissoring pair of jaws having pincer ends which are offset from a plane defined by the handles of the clamp. The clamp also includes typical handles having finger holes and a locking spacer with a ratchet and pawl type locking means. One pincer end includes a single tine which has a pivot tip normal to the length of its arm which fixes the triquetral, and the other pincer end has an L-bracket with a pair of tines that support the capitate. After the surgeon grabs these carpals with the clamp, he or she can twist the clamp depressing the capitate palmarly which in turn causes the lunate to rotate and move dorsally so as to help reduction into a preferred position for fusion.

In various embodiments, the reduction recess (or recesses) is located at the convex side of the crescent profile of the plate. In the first embodiment, which includes a single reduction recess, the recess defines a well comprising a side wall that extends downward from the top surface of the plate (as in an edge where the well is minimized to an encircling receptacle or angled wall having greater real estate for the screw holes). A bottom wall is offset from the top surface of the plate and has an edge or rim which surrounds the through hole for the lag screw and which advantageously engages the bone underneath in use to help secure that bone in place relative to the screw. The bottom wall supports the back side of the reduction or lag screw head in use and helps to define the angle provided by the screw relative to the top surface of the plate which supports or is supported by the other carpal bones (i.e. the capitate, the hamate, and the triquetrum) while the reduction screw fastens the lunate relative to the remainder of the construct. The bottom edge of the pendulous screw holes fix the hamate in position relative to the lunate, preferably by bearing on the bottom edge of a recess that is reamed into the hamate to accommodate the screw hole receiver edge.

In this embodiment, the first and second ends of the arc-shaped plate are held in position on the capitate on one side and the triquetrum on the other. In various embodiments shown, the entry position of the lag screw is defined according to the placement of the reduction recess on the arc at the convex side of the plate so that the proximal end of the screw can be nearer the end of the plates at the capitate, or the triquetrum or in the center at the hamate. In a variation of this embodiment, the plate has two reduction recesses with openings and bottom screw walls that define the retaining areas surrounding the bottom of the screw heads for two screws (optionally facing the same or the opposite direction depending on the tension desired on the resulting construct). Also, this version is shown with threaded locking screw holes for the lag screws. The distal ends of these screws converge so as to provide increased resistance to pull-out, but as stated, could also diverge to provide a differing stability to the bone/implant construct.

In an alternative version of this plate, the reduction recesses can be located on each side of the arc with recesses defined in opposing planes, here for example 150°+/−200 apart, so as to capture the hamate as well as the lunate. In this version of the plate, a screw is provided to fix the hamate.

In a second embodiment of the plate, the plate has a tri-corner extension so that a third arm is available for one or more of the reduction recesses. More particularly, the extension has a lag screw that extends away from the center of the plate in a direction below the top (i.e., away from the bone) surface of the plate at an angle of from 75° to 60°+/−10° relative to a plane defined at the top surface of the plate, and the reduction recess also includes a second opening defined at a different angle relative to the plate Le. from 25° to 60°+/−10°, such that the angle between the two lags screws in position is from 75° to 110°. Preferably, these screws are fixed angle locking screws, as are the end screws. The screw holes can include grooves, such as guide grooves.

The invention relates to the plates described, to the clamp having offset arms designed to grab and twist the carpals, and to the procedure that incorporates the plate and clamp both of which are used individually to help with fragment reduction for a bone fusion.

The invention provides a bone fusion plate that can be used in the fusion of the carpals to achieve "four corner fusion" meaning that the lunate, the triquetral, the capitate and the hamate are secured by the construct, and the hamate is pinched by the plate edge rather than by a screw in one aspect of the invention. The technique that uses the present system allows for a simple technique with fewer surgical steps than the prior art techniques. It provides for indirect reduction of the lunate which is driven by the plate. The lunate is "naked" meaning that it does not bear the plate so as to avoid impingement of the radio-lunate articulation and to preserve post-op radiographic visualization. Cross-plate screw features across the length of the plate drive lunate compression without violation of radio-lunate articulation. The procedure provides the option of K-wire free technique.

BRIEF DESCRIPTION OF THE DRAWINGS

FIG. 1 shows a fusion plate in accordance with the present invention;

FIG. 2 shows the fusion plate of FIG. 1 from a first end view;

FIG. 3 shows the fusion plate of FIG. 1 from a side on view;

FIG. 4 shows the fusion plate of FIG. 1 in position on the dorsal side of the carpal bones of a right human hand;

FIG. 34 shows a top side view of the clamp of the present invention;

FIG. 35 shows an end on view of the clamp of the FIG. 34;

FIG. 36 shows a top view of the clamp of FIG. 34 in use in the reduction of a lunate bone in accordance with an aspect of the invention;

FIG. 44 is a dorsal view of the assembly of FIG. 43;

FIG. 45 is a top front view of the plate with three screws in position in the screw holes and a front compression hole empty to illustrate a locking screw feature;

FIG. 46 is a side view of the plate in cross section through one of the compression holes; and FIG. 47 is a bottom view of the plate of FIG. 46.

DETAILED DESCRIPTION OF THE INVENTION

Figure 5:
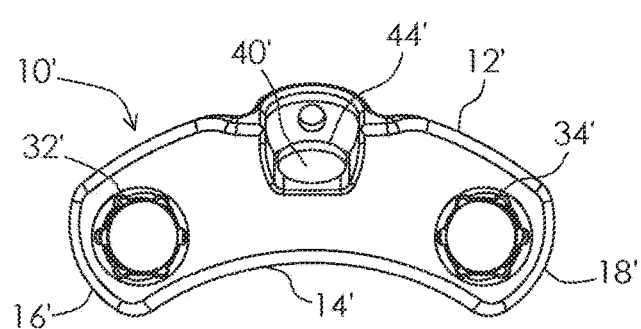
FIG. 5 shows a second version of the embodiment of the plate of FIG. 1.
Figure 6:
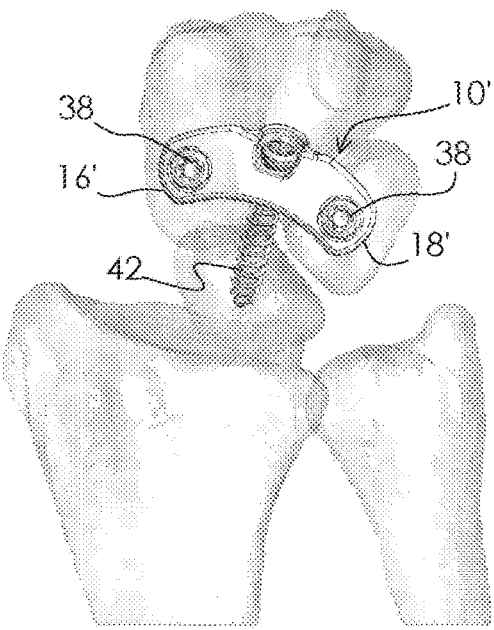
FIG. 6 shows the plate of FIG. 5 in position on the dorsal side of the carpal bones of a right human hand.
Figure 7:
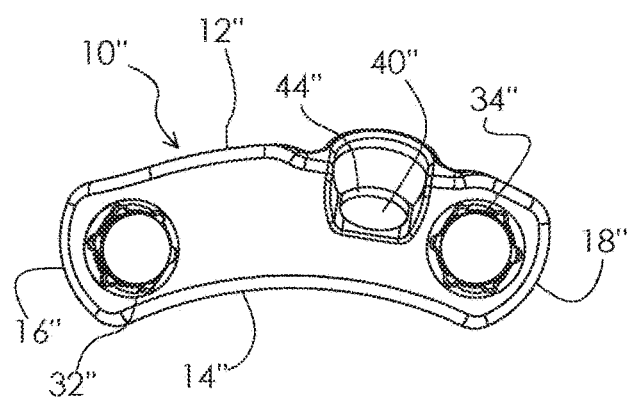
FIG. 7 shows a third version of the embodiment of the plate of FIG. 1.
Figure 8:
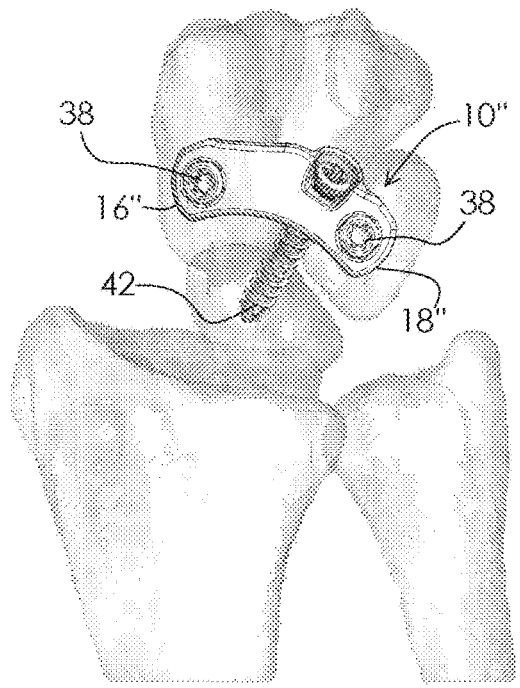
FIG. 8 shows the plate of FIG. 7 in position on the dorsal side of the carpal bones of a right human hand.
Figure 9:
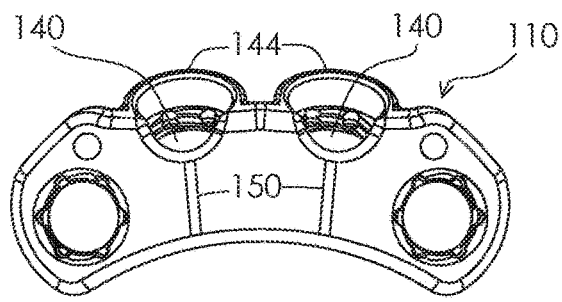
FIG. 9 shows a top view of second embodiment of the plate of the present invention.
Figure 10:
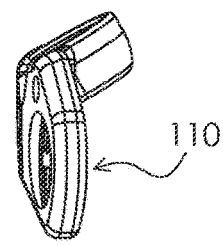
FIG. 10 shows a first end view of the plate of FIG. 9.
Figure 11:
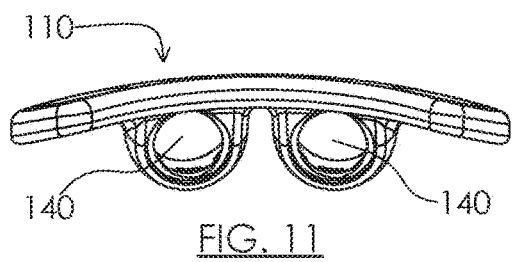
FIG. 11 shows a side view of the plate of FIG. 9.
Figure 12:
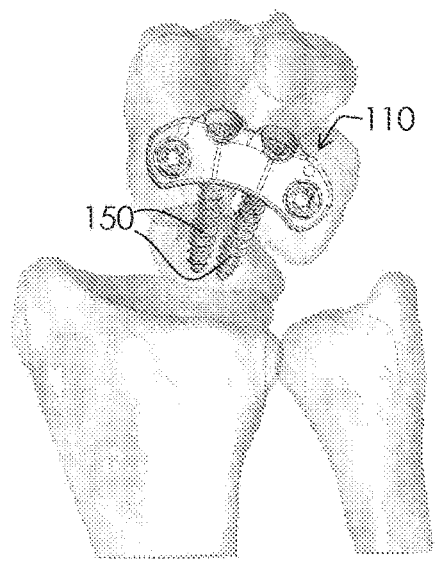
FIG. 12 shows a view of the plate of FIG. 9 in position on the dorsal side of the carpal bones of a right human hand.
Figure 13:
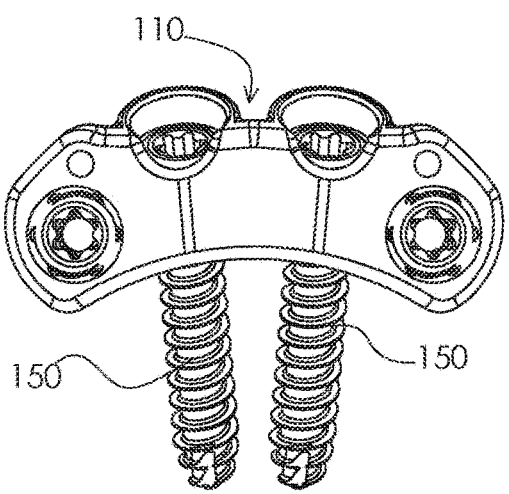
FIG. 13 shows the plate of FIG. 9 from the top with four locking screws.
Figure 14:
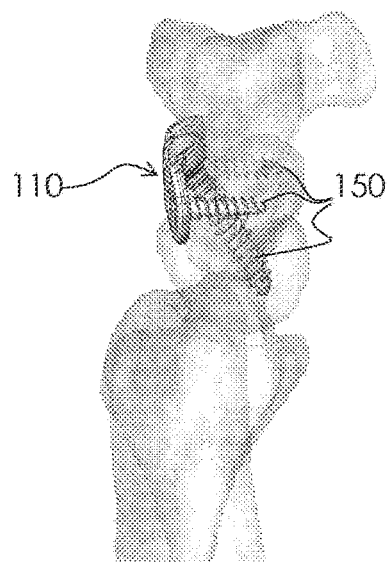
FIG. 14 shows a side view of the plate of FIG. 9 in position on the dorsal side of the carpal bones of a right human hand from the lateral side.
Figure 15:
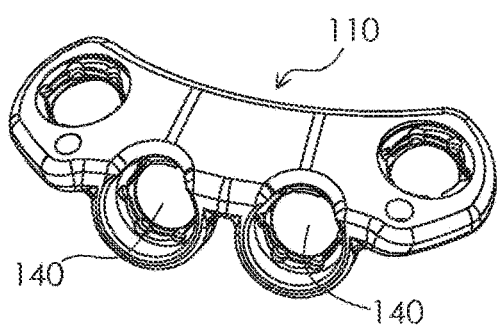
FIG. 15 shows a top side view of the plate of FIG. 9.
Figure 16:
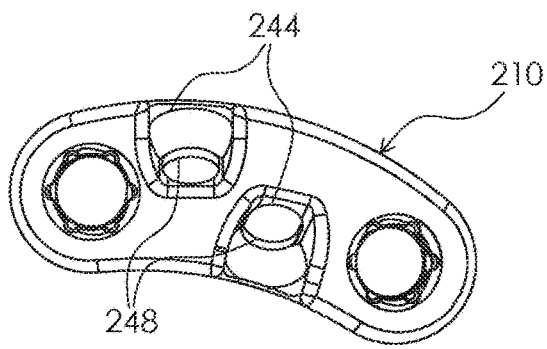
FIG. 16 shows a top view of third embodiment of the fusion plate of the present invention.
Figure 17:
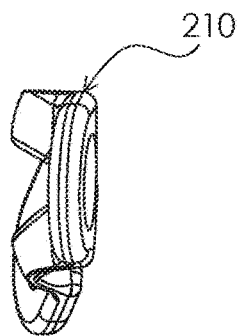
FIG. 17 shows an end view of the plate of FIG. 16.
Figure 18:
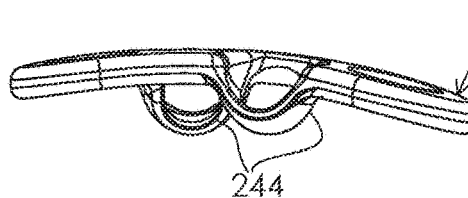
FIG. 18 shows a side edge view of the plate of FIG. 16.
Figure 19:
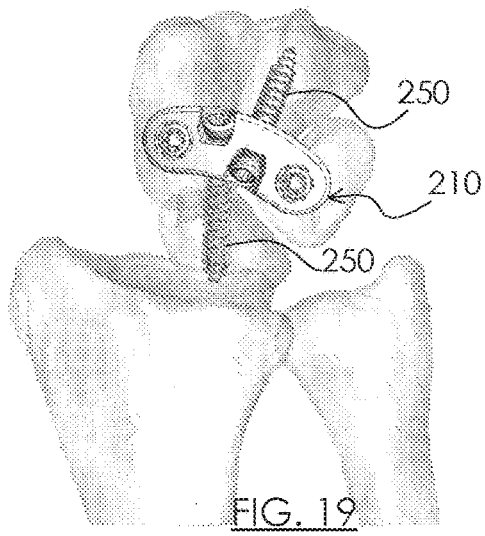
FIG. 19 shows a top view of the plate of FIG. 16 in position on the dorsal side of the carpal bones of a right human hand.
Figure 20:
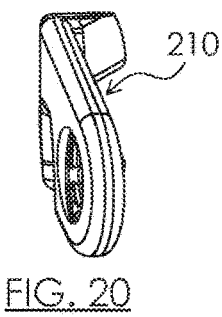
FIG. 20 shows a second end view of the plate of FIG. 16.
Figure 21:
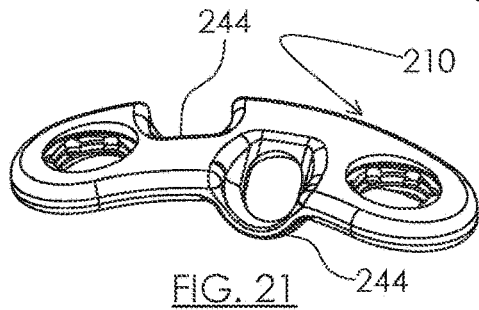
FIG. 21 shows a top side view of the plate of FIG. 16.
Figure 23:
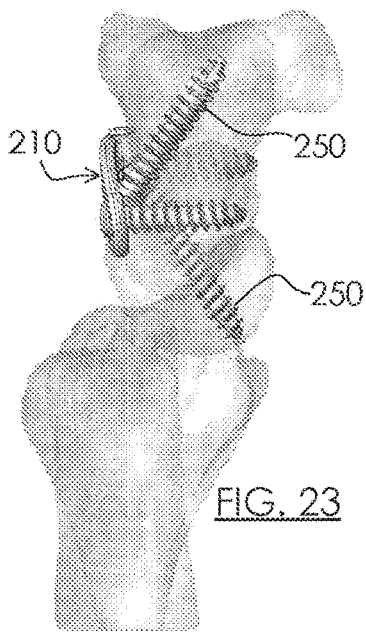
FIG. 23 shows the plate and screw assembly of FIG. 16 in the dorsal position on the carpal bones of a right human hand and taken from the lateral side view.
Figure 22:
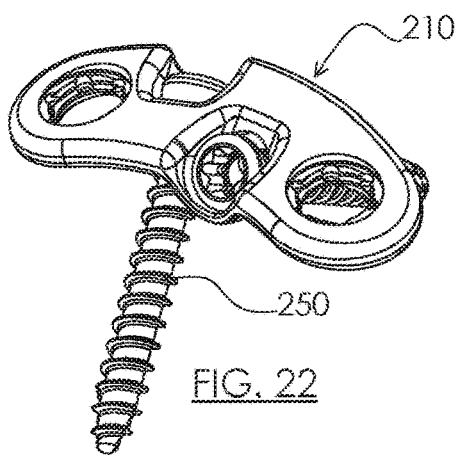
FIG. 22 shows a top side view of the plate of FIG. 16 including center lag screws in position.
Figure 24:
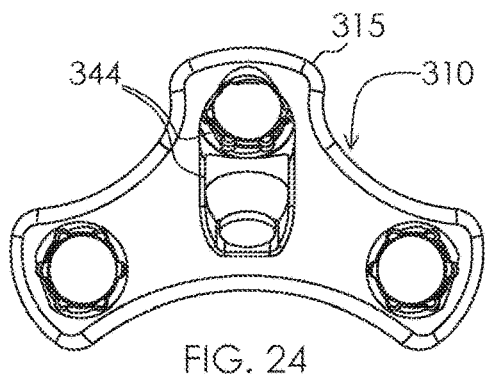
FIG. 24 shows a top view of a fourth embodiment of a plate in accordance with the present invention.
Figure 27:
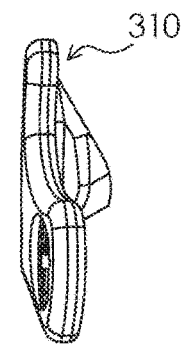
FIG. 27 shows a first end view of the plate of FIG. 24.
Figure 25:
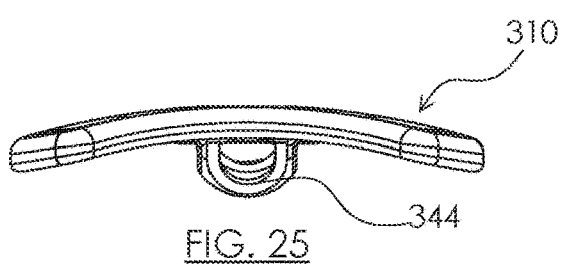
FIG. 25 shows a side view of the plate of FIG. 24.
Figure 28:
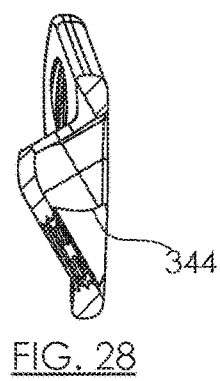
FIG. 28 shows a cross-section of the plate of FIG. 24 taken along the line A-A in FIG. 16.
Figure 26:
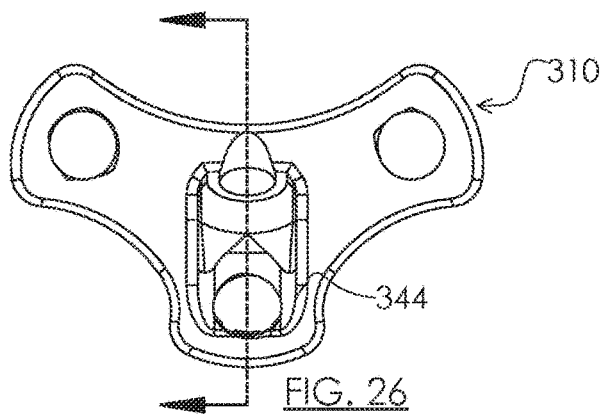
FIG. 26 shows the bottom view of the plate of FIG. 24.
Figure 29:
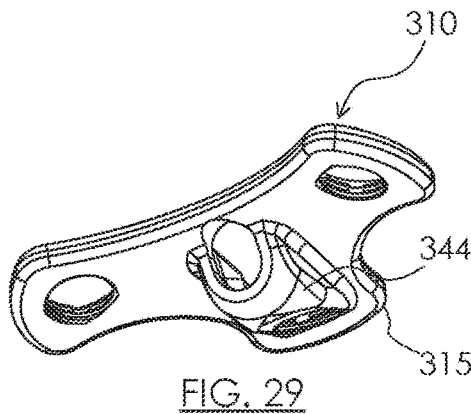
FIG. 29 shows a bottom side view of the plate of FIG. 24.
Figure 30:
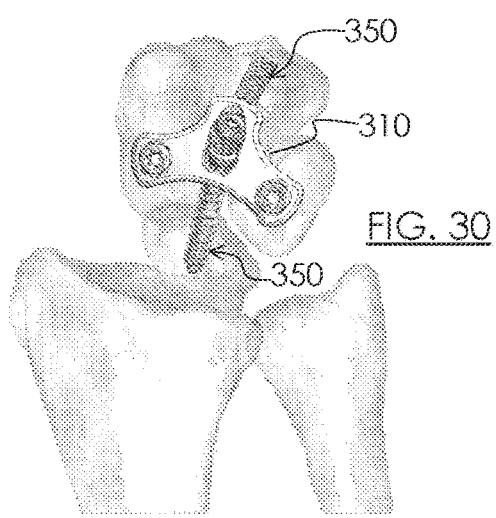
FIG. 30 shows a top view of the plate of FIG. 24 in position on the dorsal side of the carpal bones of a right human hand.
Figure 31:
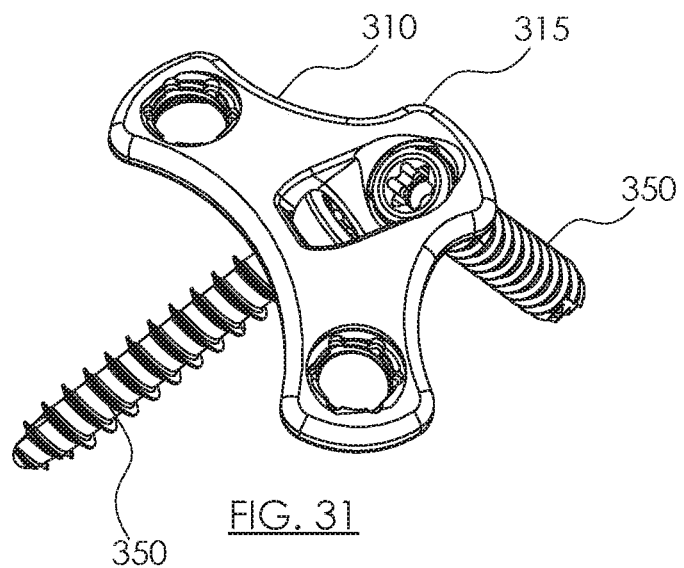
FIG. 31 shows a top view of the plate of FIG. 24 with the center lag screws in position.
Figure 32:
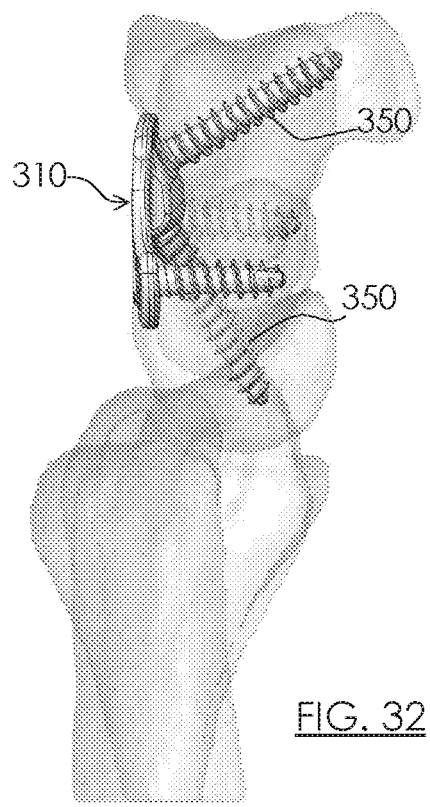
FIG. 32 shows the plate of FIG. 24 in position on the dorsal side of the carpal bones of a right human hand and viewed from the lateral side.

The present invention relates to an orthopedic implant 10, and more specifically, a plate that is crescent or arcuate shaped in outline with a convex side 12 and a concave side 14 each extending between a first radiused end 16 and a second radiused end 18 and has generally coextensive (meaning that there is a relatively constant thickness 22 therebetween and which may include a curve or topography that is planar or curved in one or more dimensions) top 24 and bottom 26 surfaces (relative to the bone) where the thickness is sufficiently substantial to support the forces that can be applied to a human hand during use and in healing so as to support the bones during fusion. The plate includes a plurality of fixation holes 30, such as first 32 and second 34 tapered threaded or otherwise locking screw holes in a first end of the arc and a second end of the arc that receives locking screws 38. The FIGS. illustrate three version of the plate, 10, 10' and 10" in which the reference numerals are differentiated also by the use of o', and o" for the variations in the compression hole well 44, 44' and 44".

The implant of the present invention is a crescent or kidney shape (i.e. a plate having an arcuate foot-print and a uniform through thickness through-out at least half of the surface area of its body and co-planar top and bottom surfaces perforated by one or more through openings which are preferably threaded so as to accept locking screws) of appropriate length (i.e. 2-3 cm), width (i.e. 5-20 mm) and thickness (i.e. 1-3 mm). In addition, the plate includes a recessed screw opening 40 that receives and supports one or more screws 42 (typically self-tapping, locking or non-locking threaded cancellous screws of from 10 to 40 mm in length), such as a lag screw, at an oblique angle relative to the plane of the top surface. This screw can be used for the compression or reduction of a bone or bone fragment, often preferably the lunate in wrist fusion procedures.

In various embodiments, the reduction recess 44 (or recesses) is located at the convex side of the crescent profile. In the first embodiment, which includes a single reduction recess, the recess including a well comprising a side wall 46 that extends downward from the top surface of the plate (i.e. from 2 to 6 mm) and a bottom wall 48 which surrounds the through hole 40 for the lag screw. The bottom wall 48 supports the back side 50 of the reduction or lag screw head in use and helps to define the angle provided by the screw relative to the top surface of the plate which supports or is supported by the other carpal bones (i.e. the capitate, the hamate, and the triquetrum) while the reduction screw fastens the lunate relative to the remainder of the construct. The edge of the recess which contains the hole 40 forms a rim that resides in a recess countersunk into the bone to help to confine the bone into which it is set. In this embodiment, the first and second ends of the arc-shaped plate are held in position on the capitate on one side and the triquetrum on the other. In various embodiments shown, the entry position of the lag screw is defined according to the placement of the reduction recess on the arc at the convex side of the plate so that the proximal end of the screw can be nearer the end of the plates at the capitate, or the triquetrum or in the center at the hamate.

In a variation of this embodiment shown in FIGS. 9-14, the plate 110 has two reduction recesses 144 with openings 140 and bottom screw walls 148 that define the retaining areas 248 surrounding the bottom of the screw heads for two screws 250. Here, the side walls of the reduction recesses form conjoined circular rims that form a teeth shape to provide better leverage in the underlying bone. Also, this version is shown with threaded locking screw holes for the lag screws 150. The distal ends of these screws converge so as to provide increased resistance to pull-out. The plate is also illustrated including a pair of laser etched lines 150 that are aligned with the reduction recesses and can be used to help orient the plate.

The plate has a length which is between 0.5 and 1.5 inches, a width of from 0.2 and 0.75+/−0.01 inches, a thickness of 0.04 to 0.3+/−0.05 inches and the compression screw wells have a depth of from 0.1 to 0.25+/−0.05 inches.

In an alternative version of this plate 210, the reduction recesses 244 can be located on each side of the arc with recesses 244 defined in opposing planes, here for example 150°+/−20° apart, so as to capture the hamate as well as the lunate.

In a second embodiment of the outline of the plate, the plate 310 has a tri-corner extension so that a third arm 3i 5 is available for one or more of the reduction recesses 344. More particularly, the extension has a lag screw 350 that extends away from the center of the plate in a direction below the top (i.e., away from the bone) surface of the plate at an angle of from 75° to 60°+/−10° relative to a plane defined at the top surface of the plate, and the reduction recess also includes a second opening defined at a different angle relative to the plate i.e. from 15° to 45°+/−10°, such that the angle between the two lags screws in position is from 75° to 120°. Preferably, these screws are fixed angle locking screws, as are the end screws.

Figure 33:
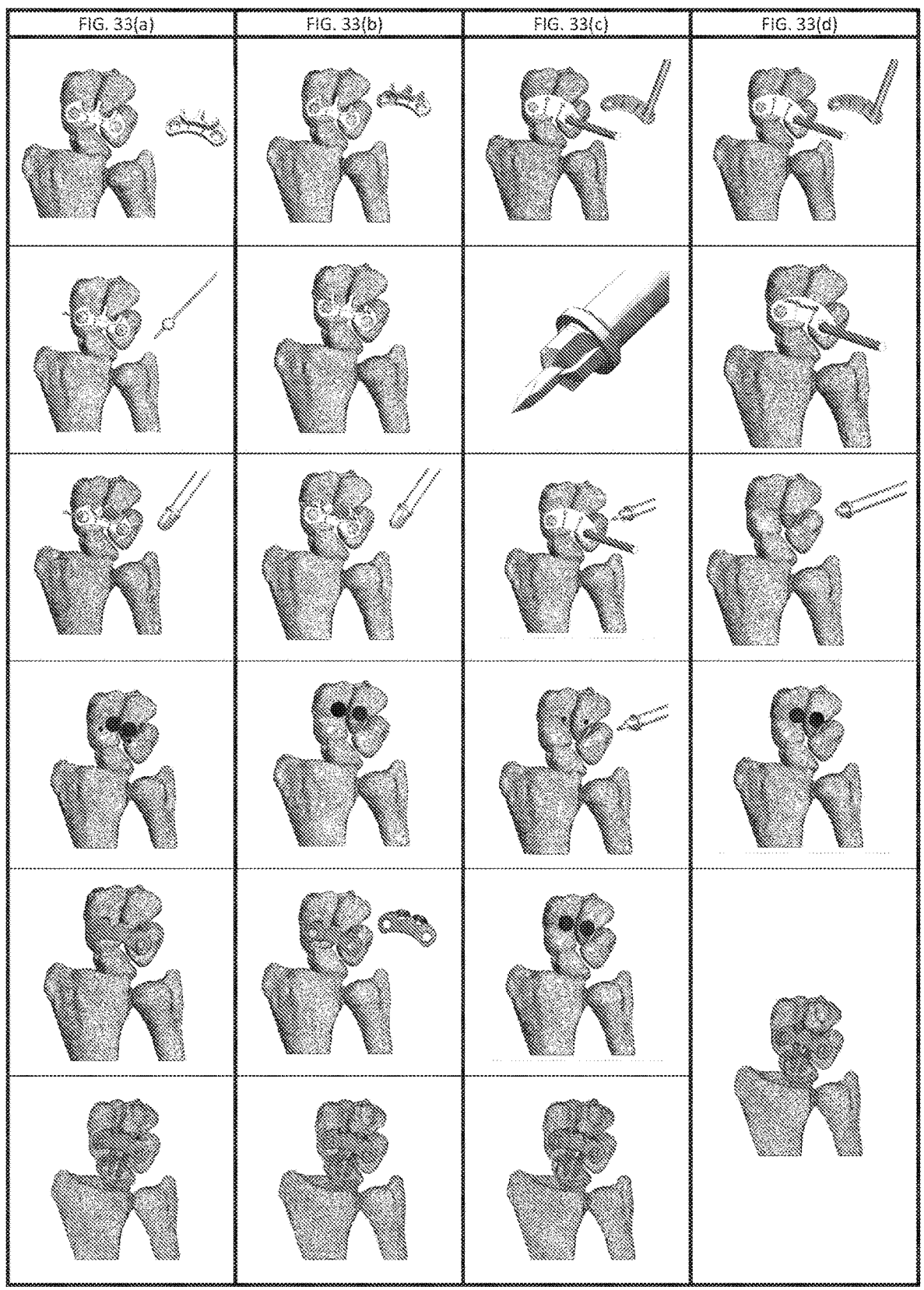
FIG. 33 illustrates four different surgical methods for using a template to mark the location of the fusion plate and to prepare the bone and to implant the fusion plate in a human wrist in accordance with the invention.

FIG. 33 illustrates four methods of wrist fusion that use the system of the present invention. In FIG. 33(a), the template is secured using olive wires, while the template is secured with k-wires in FIG. 33(b), and in FIG. 33(c) a starter tip reamer is used, while a cannulated reamer is used in FIG. 33(d).

In the first procedure as illustrated the carpals are prepared for the fusion with a dorsal exposure of the carpal area. The scaphoid bone is excised and a special clamp having offset arms is used to reduce the lunate by grasping the outer carpals, the triquetrium and the capitate and rotating the offset jaws of the clamp about a medial axis of the clamp so as to move the capitate palmarly which in turn causes the lunate to rotate dorsally. Once the carpals are re-positioned, the fixation procedure can begin in one of four illustrated manners. In the first one, a template 400 is positioned spanning the triquetral, and capitate with the laser guide lines directed at the lunate. Then, the template is fixed to the triquetral with an olive wire and the capitate is reduced and fixed using an olive wire. A reamer 404 is used to countersink through the template for the compression screw wells. The olive wires and template are removed, and the plate is positioned ensuring that the laser marks are directed at the lunate. The plate is fixed using a screw to the triquetral and then to the capitate, and then the lunate is fixed (and reduced) using compression screws through the compression screw holes such that the final reduction of the lunate can be accomplished using the plate screw system. In a second procedure, k-wires 405 are used rather than the olive wires, and the procedure is similar, except the k-wires can be used to hold the position of the reduced bones, and the template 400 is slide off the k-wires and the plate is slide onto the k-wires. In a third procedure, a template 400' is placed on the carpals with laser marks directed at the lunate and a reamer 404' having a trocar tip is used to create starter holes at the compression screw wells which are then reamed to full depth. These countersunk holes are used to position the plate which is secured as previously described. In a fourth version of the procedure, the template 400' is placed using the laser marks, and k-wires are driven through k-wire holes in the template and a cannulated reamer 404" is used over the k-wires 405 to drill holes for the end screws and at the compression screw holes. The template is removed and the plate is placed and secured.

The present involves a unique clamp 500 that has a locking scissoring pair of jaws 502 joined at a pivot point 501 and having pincer ends which are offset from a plane defined by the handles of the clamp. The clamp also includes typical handles 504 having finger holes and a locking spacer 508 with a threaded cross member 509 and locking nut 510 or a ratchet and pawl type locking means. One pincer end includes a single tine 512 which has a pivot tip normal to the length of its arm which fixes the triquetral, and the other pincer end has an L-bracket 514 with a tine 516 that supports the capitate dorsally. After the surgeon grabs these carpals with the clamp, he or she can twist the clamp to cause the capitate to move palmarly which in turn forces the lunate to rotate and move upward so as to help reduction into a preferred position for fusion.

Figure 37:
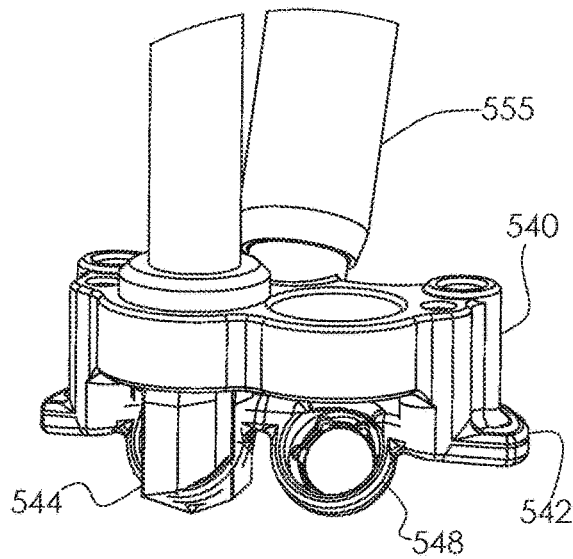
FIG. 37 shows a front edge view of a reaming guide and reamer for use in the method of the present invention.
Figure 38:
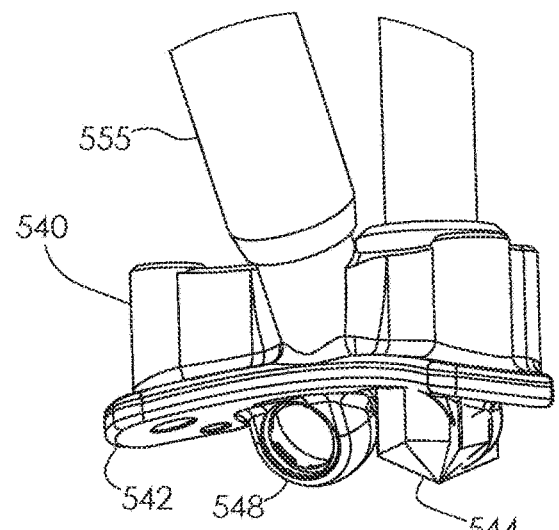
FIG. 38 is a back view of the reaming guide and reamer of FIG. 37.
Figure 39:
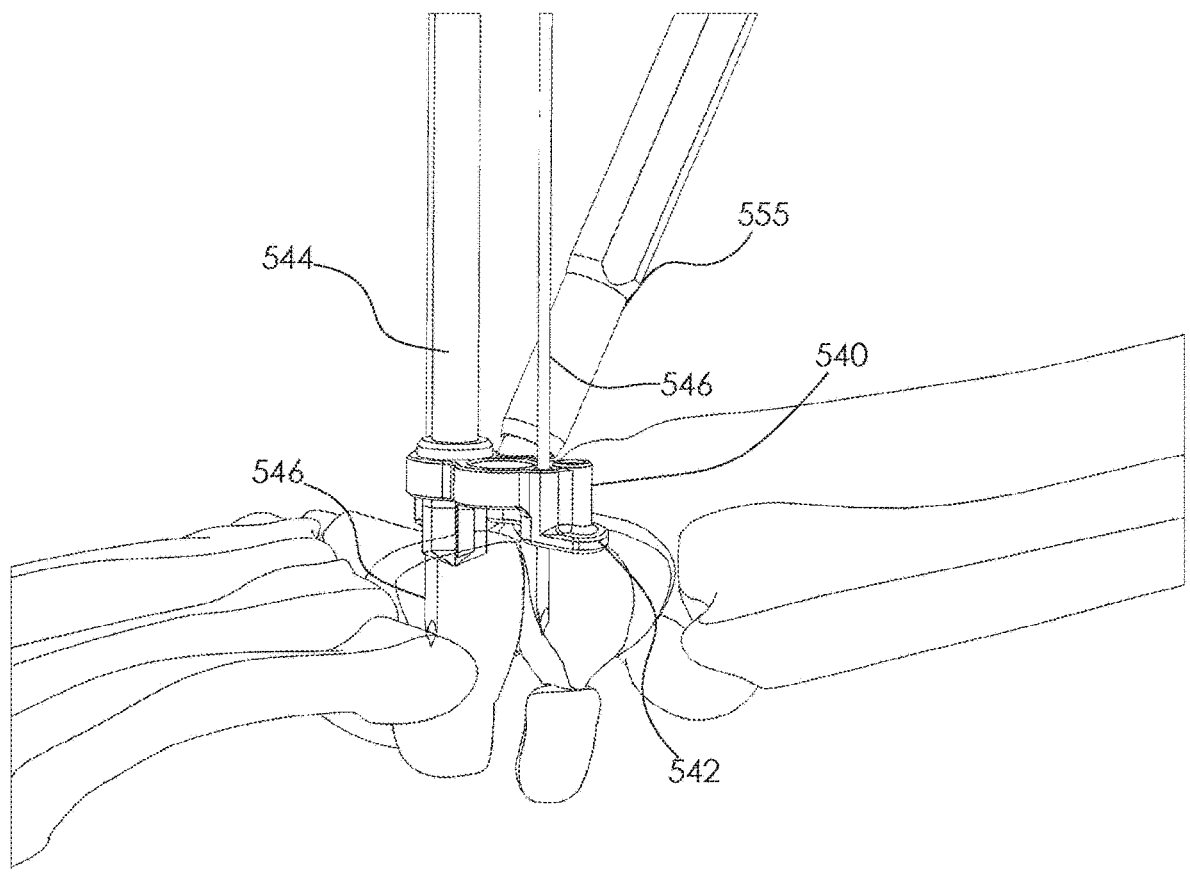
FIG. 39 is a view of the reaming guide and reamer of FIG. 37 in place on the carpals for use in a method of the present invention.
Figure 40:
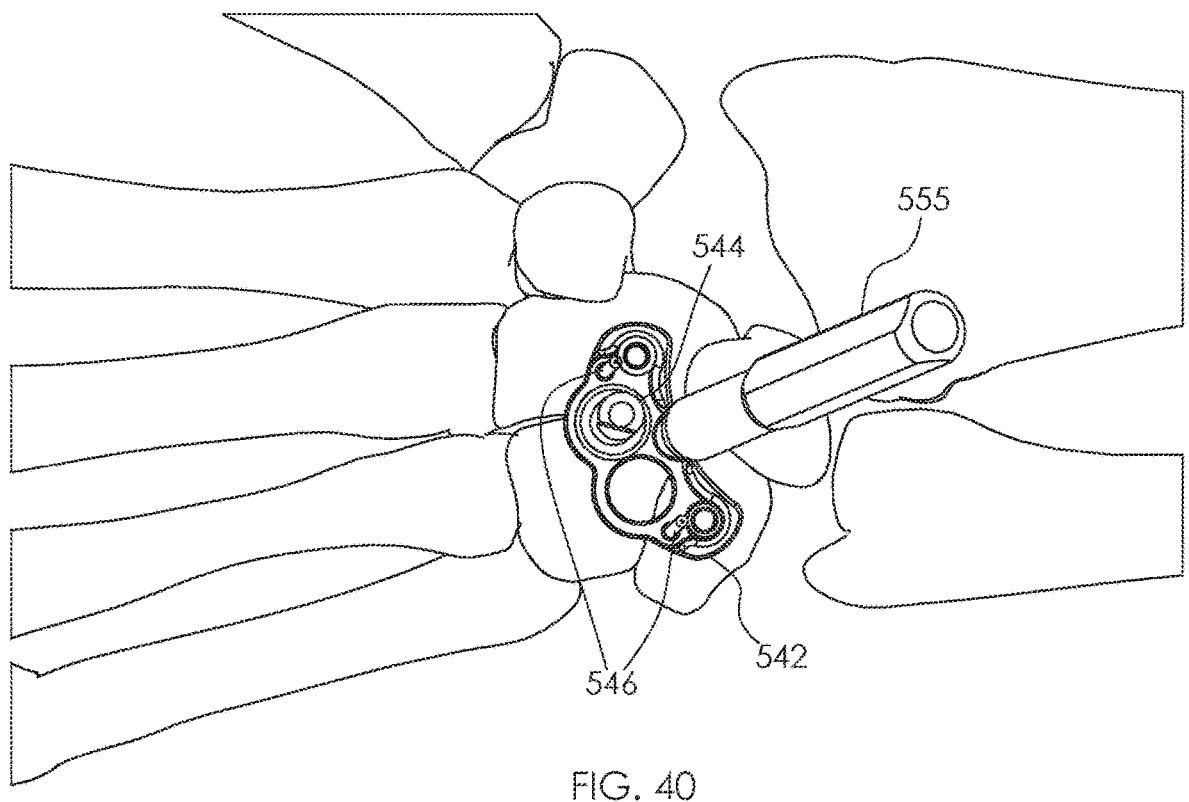
FIG. 40 is a top view of the assembly of FIG. 39.
Figure 41:
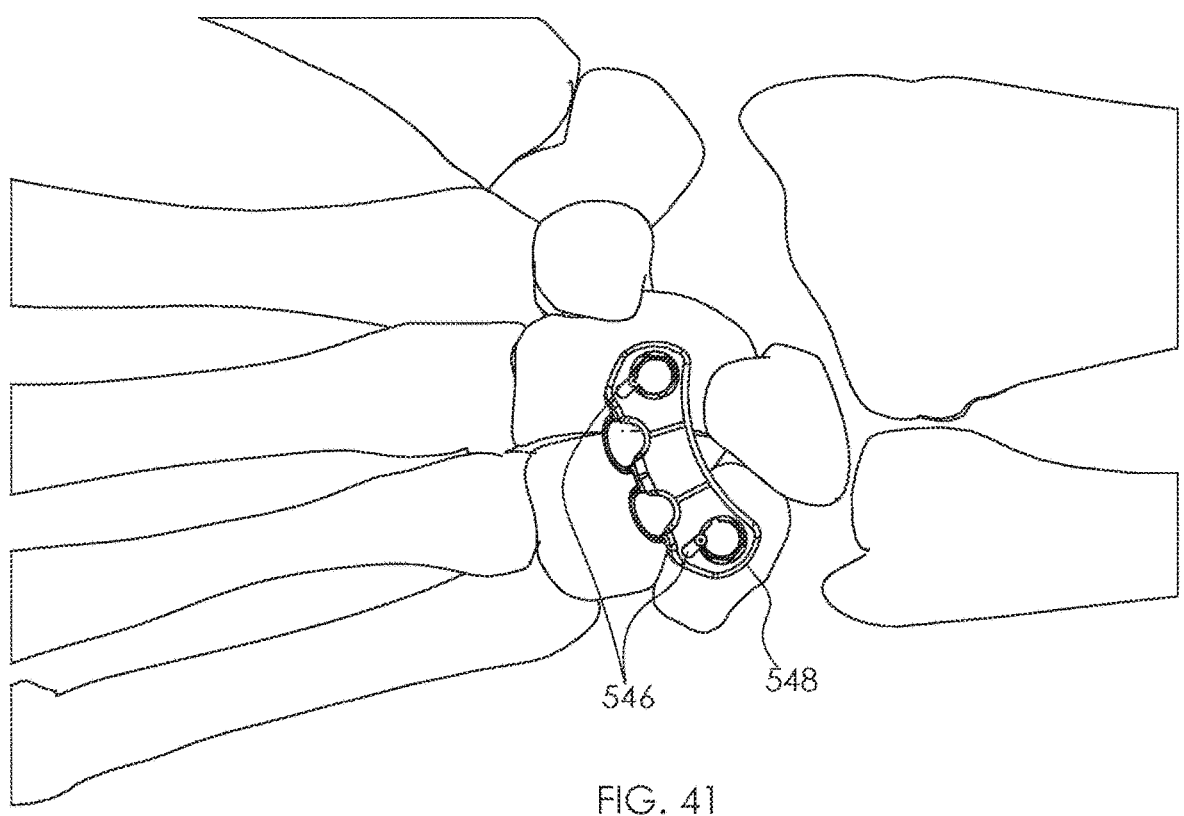
FIG. 41 shows the placement of the plate following the reaming step.
Figure 42:
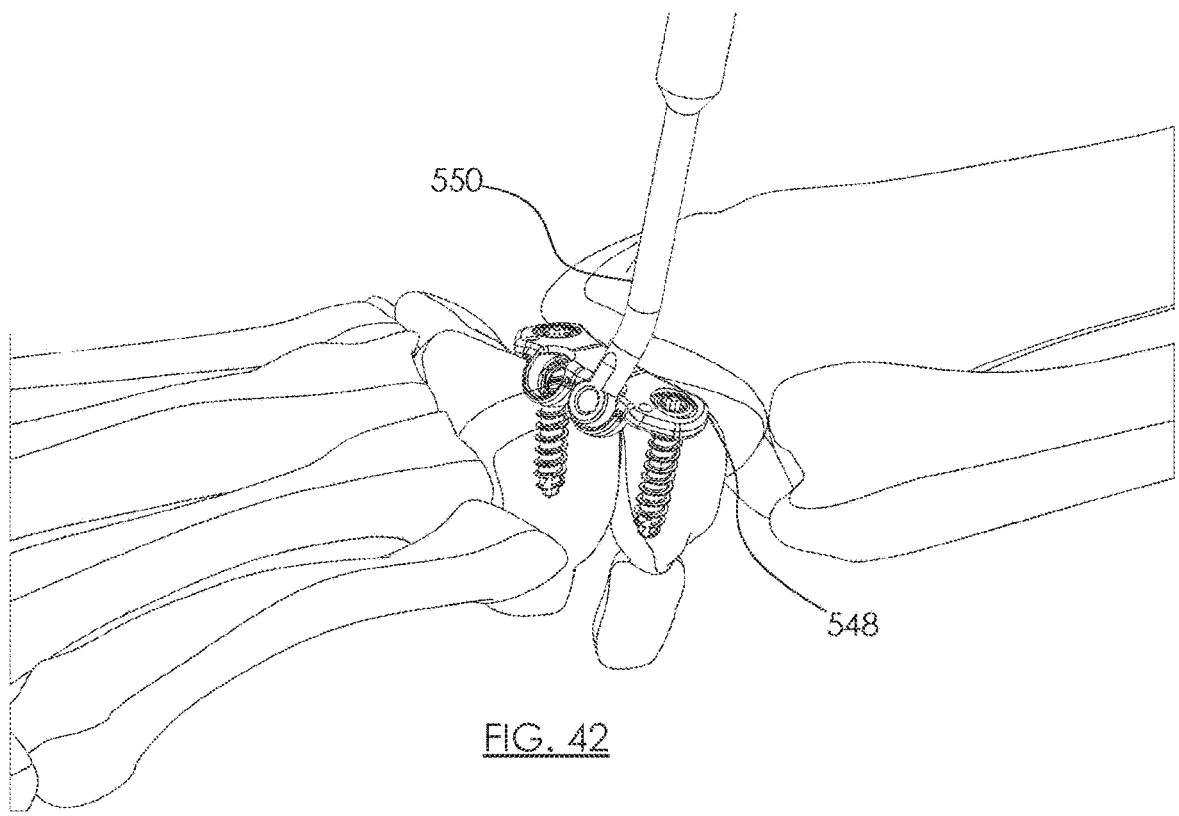
FIG. 42 shows the use of a drill guide in the edge holes of the plate of the present invention.

FIGS. 37, 38, and 39 illustrate a reamer guide 540 with a plate template 542 and handle 555 and with a reamer 544 engaged in one of the compression/reduction screw holes of the guide. FIG. 37 shows the reamer-template assembly from the front view overlaid with the plate 548 to illustrate how the reamer and template are shaped to match the plate shape. FIG. 38 shows the assembly of FIG. 37 from the back view, and FIG. 39 shows the assembly on a wrist from the side with k-wires 546. Following the reaming step, the reaming guide is removed by sliding it off the k-wires and a plate 548 is positioned over the k-wires 546 as is shown in FIG. 41. FIG. 42 shows a plate 548 in position with the reduction holes positioned into the counterbores which have been reamed out, and a drill guide 550 in position for the reduction screws.

Figure 43:
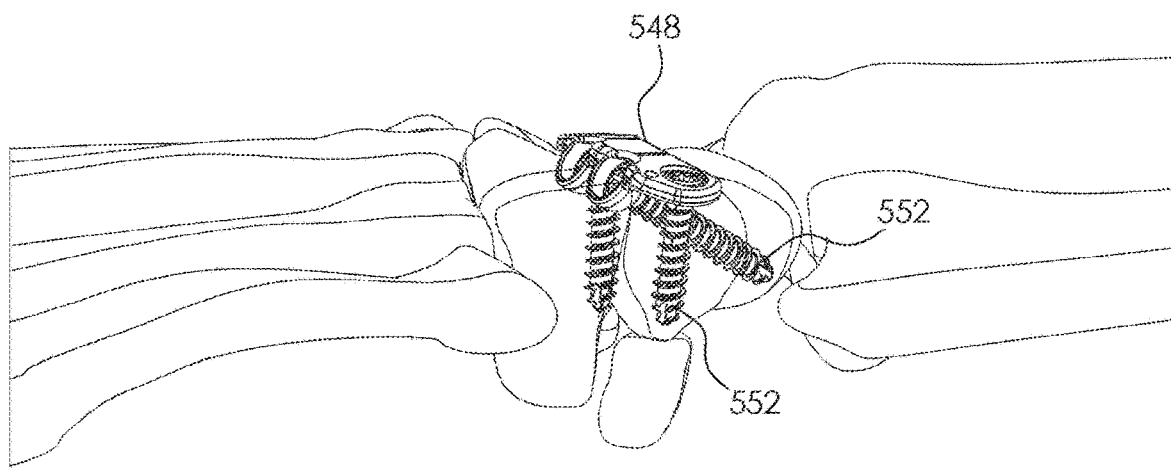
FIG. 43 shows a lateral side view of the plate and screws in place on a wrist.

FIGS. 43 and 44 illustrate a side and top view of the plate 548 with screw assembly after the screws 552 have been implanted through the plate, and for clarity, FIG. 45 shows the plate 548 in a plate assembly 558 (minus one reduction screw 556 but with both of the end screws 559). This view illustrates a variable locking mechanism 560 which includes interruptions 561 in the threads 563 of the screw holes 564 which allow a threaded screw head 565 to bear against the threads 562 and wedge into a variable locking relationship. FIG. 46 shows a cross-section of the plate taken through a reduction hole in order to illustrate the configuration of the screw holes 564. FIG. 47 is a view from the bottom side of the plate.

What is claimed is:

1. An orthopedic fusion plate assembly, comprising:
   a plate having top and bottom surfaces, the plate including:
   a first end comprising a first screw hole and a second end comprising a second screw hole, wherein the first end and the second end are at opposing ends of the plate,
   a convex side connecting a first side of the first end and a first side of the second end,
   a concave side connecting a second side of the first end and a second side of the second end, and
   a recess having a side wall and a bottom wall, wherein the side wall extends from the top surface of the plate, wherein the bottom wall includes an opening which is not within the top or bottom surfaces of the plate, and wherein the opening is positioned to receive a screw to draw a bone or bone fragment in a direction of the bottom surface of the plate.

2. The orthopedic fusion plate assembly as set forth in claim 1, wherein the recess is located at the convex side of the plate.

3. The orthopedic fusion plate assembly as set forth in claim 1, wherein an outline of the top surface of the plate has a crescent shape.

4. The orthopedic fusion plate assembly as set forth in claim 3, wherein the intermediate offset recess is midway between the first and second ends of the plate.

5. The orthopedic fusion plate assembly as set forth in claim 3, wherein the recess is closer to the first end than the second end of the plate.

6. The orthopedic fusion plate assembly as set forth in claim 1, wherein the recess is opposite the concave side of the plate.

7. The orthopedic fusion plate assembly as set forth in claim 1, wherein the intermediate offset recess comprises at least two intermediate offset recesses.

8. The orthopedic fusion plate assembly as set forth in claim 1, wherein the plate is configured to be implanted on a wrist.

9. The orthopedic fusion plate assembly as set forth in claim 1, wherein the first screw hole and the second screw hole each comprise a thread.

10. The orthopedic fusion plate assembly as set forth in claim 1, wherein the opening of the bottom wall of the recess is at an oblique angle relative to a plane of the top surface.

11. The orthopedic fusion plate assembly as set forth in claim 1, wherein the plate comprises a uniform thickness through-out at least half of the plate.

12. The orthopedic fusion plate assembly as set forth in claim 1, wherein a length of the plate from the first end of the plate to a second end of the plate is between 2 cm and 3 cm.

13. The orthopedic fusion plate assembly as set forth in claim 1, wherein a width of the plate is between 5 mm and 20 mm.

14. The orthopedic fusion plate assembly as set forth in claim 1, wherein a thickness of the plate from the top surface to the bottom surface is between 1 mm and 3 mm.

15. The orthopedic fusion plate assembly as set forth in claim 1, wherein the first screw hole is configured to be positioned on a capitate and the second screw hole is configured to be positioned on a triquetrum.

* * * * *